United States Patent [19]

Hikino et al.

[11] Patent Number: 4,598,069
[45] Date of Patent: Jul. 1, 1986

[54] METHOD OF TREATING HYPOGLYCEMIA USING ALOES POLYSACCHARIDES

[75] Inventors: Hiroshi Hikino, Sendai; Teruaki Hayashi, Kawanishi, both of Japan

[73] Assignee: Toyo Yakushoku Kogyo Co. Ltd., Tokyo, Japan

[21] Appl. No.: 718,082

[22] Filed: Apr. 1, 1985

[30] Foreign Application Priority Data

Apr. 5, 1984 [JP] Japan ................................. 59-67943

[51] Int. Cl.$^4$ ........................................... A61K 31/715
[52] U.S. Cl. ...................................... 514/54; 536/1.1; 536/128
[58] Field of Search ................ 536/1.1, 114, 124, 128, 536/123; 514/54

[56] References Cited

U.S. PATENT DOCUMENTS 3,360,511 12/1967 Farkas .................................. 536/114
3,470,109 9/1969 Marsh, Jr. ............................. 536/1.1

OTHER PUBLICATIONS

Rakhimov et al., "Chem. Abst.", vol. 86, 1977, P 86,163(r).
Rakhimov et al., "Chem. Abst.", vol. 94, 1981, P 136,159(g).

Primary Examiner—Johnnie R. Brown
Attorney, Agent, or Firm—Stiefel, Gross, Kurland & Pavane

[57] ABSTRACT

A hypoglycemic composition which contains as an effective component a polysaccharide contained in aloes of the family Liliaceae and having hypoglycemic activity and water solubility, and a method of treating diabetes comprising administering to a patient afflicted with diabetes a theraputically effective amount of the above composition.

5 Claims, No Drawings

METHOD OF TREATING HYPOGLYCEMIA USING ALOES POLYSACCHARIDES

BACKGROUND OF THE INVENTION

1. Field of the Invention

The present invention relates to a hypoglycemic composition comprising as its effective component a polysaccharide having hypoglycemic activity which lowers blood glucose value and contained in aloes which are plants of the family Liliaceae.

2. Description of the Prior Art

It is well known that a crude drug prepared from aloes of the family Liliaceae is used as a laxative [Japanese Pharmacopeia, 9th edition, (1976), D-55], whereas other medicinal efficacies thereof still remain to be clarified.

SUMMARY OF THE INVENTION

We have found that a crude drug from aloes has hypoglycemic activity and further conducted research. As a result, we obtained hypoglycemic polysaccharides from the water-soluble component of aloes of the family Liliaceae by dialyzing the soluble components to remove the substances up to 24 angstroms in particle size. Thus, the present invention has been accomplished.

Although the characteristics of the polysaccharides obtained differ slightly according to the kind of aloe used as the material, any of these polysaccharides has the following unique properties.

(i) Solubility in water.

(ii) Hypoglycemic activity.

(iii) Developing a pale yellowish red color when brought into contact with a mixture of 2% aqueous solution of phenol and concentrated sulfuric acid, and being positive when subjected to silver mirror reaction or exposed to Fehling's solution (testing for polysaccharides).

(iv) Being larger than 24 angstroms in particle size.

Thus, the present invention provides a hypoglycemic composition comprising as its effective component a polysaccharide which has hypoglycemic activity and is a water-soluble component of aloes of the family Liliaceae, and a method of treating diabetes comprising administering to a patient afflicted with diabetes a therapeutically effective amount of the above composition.

DESCRIPTION OF THE PREFERRED EMBODIMENTS

Given below are aloes of the family Liliaceae which contain the polysaccharides of the present invention.

An arborescent aloe (*Aloe arborescens Mill.*), cape aloes (*Aloe ferox Mill., Aloe vera L.* and *Aloe africana Mill.*), nathal aloes (*Aloe barberae Dyer* and *Aloe soccotrina Lam.*), a zanzibar aloe (*Aloe perryi Baker*), a curacau aloe (*Aloe barbadensis Miller*), jaffarabad aloes (*Aloe vera L. chinensis Haw.* and *Aloe striatula Haw.*), etc. Of course, *Aloe arborescens Mill* is grown recently and is a material which is readily available.

As the material of the effective component of aloes to be used in this invention, all leaves or the whole of the plane may be used in a fresh state or as dried.

The effective component may be obtained in the following manner.

First, the material, as it is or as treated for de-fatting with a usual fat-dissolving solvent such as ethyl ether, is subjected to extraction with water or an aqueous organic solvent (in 1.5 to 4 times the amount of fresh material). While the extraction can be conducted with water satisfactorily, an aqueous organic solvent may be used to prevent the extract from decaying or promote the extraction. Water and aqueous organic solvent may be used conjointly. Useful organic solvents for preparing the aqueous organic solvent are lower alcohols such as methanol and ethanol. Depending on the kind of material, etc., up to 50%, preferably up to 30%, of organic solvent is contained in the aqueous organic solvent. The extraction can be accelerated at an elevated temperature. Preferably the material is crushed or pulverized before use.

The extract obtained is dialyzed as it is or as concentrated at a reduced pressure. Alternatively, a solution is dialyzed, which is prepared by adding a lower alcohol to the extract or concentrate to precipitate the hypoglycemic component, filtering the precipitate off, washing the precipitate with ethanol and dissolving the product in water or an aqueous organic solvent. The dialysis is conducted by means of a seamless cellulose membrane tubing (36/32 type, product of Visking Company in U.S.A.) for removing substances up to 24 angstroms in particle size, using the extract, concentrate or solution as the inner liquid and water as the outer liquid (in 4 to 6 times the amount of the inner liquid). The dialysis is carried out for 2 to 3 days (while replacing the water approximately once daily). Alternatively, a solution may be dialyzed which is prepared by evaporating the extract to dryness under a reduced pressure, dissolving the residue in water and removing the insolubles from the resulting solution.

The dialyzate thus obtained is dried in a vacuum to obtain a brown powder as the active component of the present invention.

We have found that the polysaccharide thus prepared has an outstanding hypoglycemic effect as will be described later but little or no side effect.

The dosage of the hypoglycemic composition of the present invention varies with the symptom. For oral administration to adults, the composition is given usually in an amount of 10 to 500 mg/day, preferably 30 to 300 mg/day, calculated as the active component, in two to three divided doses, whereby the contemplated effect can be obtained.

The hypoglycemic composition of the present invention comprises one or a mixture of polysaccharides and a solid or liquid excipient. The composition is given orally usually in the form of a powder, tablets including sublingual tablets, emulsion, encapsulated preparation, granules, pellets, liquid preparations (including fluid extract and syrup), etc. The composition may be given in the form of an injection solution. The solid or liquid excipient to be used is one already known in the art. Preferably, each unit of the preparation contains the above-mentioned single dose of the present compound.

Examples of excipients useful for power, granular, or other oral preparations are lactose, starch, dextrin, calcium phosphate, calcium carbonate, synthetic and natural aluminum silicates, magnesium oxide, dry aluminum hydroxide, magnesium stearate, sodium bicarbonate, dry yeasts, etc.

This invention further includes cutaneously absorbable preparations formulated with use of usual excipients.

The preparations as mentioned above may be formulated by the conventional methods.

The polysaccharides of the invention are usable as health food containing the compound in an amount useful for keeping health but not producing a therapeutic effect. The compound is then given in a suitable form such as a liquid, granules, tea, usual capsules, soft capsules or the like.

The present invention will be described with reference to the following examples and animal experiment.

EXAMPLES

A 2 kg quantity of fresh *Aloe vera L.* was slightly dried in air, crushed and then immersed overnight in a mixture of about 5 liters of water and ethanol (1:1) at room temperature for extraction. The material was extracted in this manner two times, and thereafter three times similarly with use of water only. The collected extracts were filtered, and the combined filtrate was concentrated to about 2 liters in a vacuum by evaporating the solvent off. (If the filtrate bubbles up, a small amount of n-butanol is added.) The concentrate obtained was filtered to remove the insolubles. The filtrate was placed into a cellulose dialyzing membrane, (36/32 type, manufactured by Visking Company, and dialyzed for 3 days using about 10 liters of water as the outer liquid. (The outer liquid was replaced at least once daily.) The resulting dialyzate (inner liquid) was distilled in a vacuum to remove the solvent and then dried overnight in a desiccator, giving a brown powder (4.9 g). The product is a polysaccharide having the following properties and also having the hypoglycemic activity to be stated later.

(i) Infrared absorption spectrum (KBr method) $\nu$max: 3370, 1730, 1600, 1235 and 1040 cm$^{-1}$ (ii) Ultraviolet absorption: $\lambda_{max}^{H2O}$ 275 nm; $E_1\, _{cm}^{0.05\%}$: 12; $\lambda_{max}^{H2O}$ 295 nm; $E_1\, _{cm}^{0.05\%}$: 12

(iii) NMR spectrum (90 MHz, D$_2$O): 5.12(s), 5.03–4.64(m), 4.59(s), 4.43(s), 4.13(s), 3.49(s), 2.05(s), 1.88(s), 1.49(s) and 1.27(d, j=7)

(iv) pH: Having a pH of 4.75 when 100 mg of the product is dissolved in 10 ml of distilled water.

(v) Decomposition temperature: 240° C.

(vi) Solubility: Being soluble in water and insoluble in benzene, ether, chloroform, alcohols and acetone.

(vii) Color reaction: Developing a pale yellowish red color on contact with a mixture of 2% aqueous solution of phenol and concentrated sulfuric acid, and being positive for silver mirror reaction and Fehling's solution.

A brown powder was prepared from *Aloe arborescens Mill.* in the same manner as above. The product is also a polysaccharide having the following properties and further having the hypoglycemic activity to be stated later.

(i) Infrared absorption spectrum (KBr method) $\nu$max: 3300, 1590, 1410, 1240, 1050 and 600(broad) cm$^{-1}$ (ii) Ultraviolet absorption $\lambda_{max}^{H2O}$ 275 nm; $E_1\, _{cm}^{0.01\%}$: 50; $\lambda_{max}^{H2O}$ 305 nm; $E_1\, _{cm}^{0.01\%}$: 50

(iii) NMR spectrum (90 MHz, D$_2$O): 5.25(s), 5.21—4.35(m), 4.21(s), 3.92–3.45(m), 2.39(s), 2.07(s), 1.85(s), 1.50(s), 1.25(s)

(iv) pH: Having a pH of 4.95 when 100 mg of the product is dissolved in 10 ml of distilled water.

(v) Decomposition temperature: 240° C.

(vi) Solubility: Being soluble in water and insoluble in benzene, ether, chloroform, alcohols and acetone.

(vii) Color reaction: Developing a pale yellowish red color on contact with a mixture of 2% aqueous solution of phenol and concentrated sulfuric acid, and being positive for silver mirror reaction and Fehling's solution.

Test for Pharmacological Effect

Mice(Std. ddY strain, weighing 25 to 30 g) were divided into groups each consisting of 5 mice. The blood of each mouse was collected from the vein of the fundus oculi by a hematocrit tube and immediately centrifuged at 12000 r.p.m. for 5 minutes to obtain plasma. With use of glucose analyzer (Iatron M-7000, product of Dia-Iatron Co., Ltd.), the amount of glucose in the plasma was measured as the blood glucose value before the administration of the test specimen (0 hr.). Immediately after the collection of blood at 0 hr., a solution of the test specimen dissolved in physiological saline was intraperitoneally given to the mouse.

Seven hrs. and 24 hrs. after the administration of the specimen, the blood was collected, the amount of glucose in the plasma was measured, and the blood glucose value was calculated relative to that of 0 hr. which was taken as 100. The results are shown in Table 1, in which each relative value is expressed in average±standard error. The significance difference was determined by one-way variance analysis.

TABLE 1

| Test specimen | Dose (mg/kg) | Relative blood glucose value | | |
|---|---|---|---|---|
| | | 0 hr. | 7 hrs. | 24 hrs. |
| Control | 0 | 100 | 115 ± 6.8 | 110 ± 7.3 |
| Polysaccharide of *Aloe vera L.* prepared above | 100 | 100 | 66 ± 4.9*** | 87 ± 8.5 |
| Polysaccharide of *Aloe arborescens Mill* prepared above | 100 | 100 | 54 ± 2.8*** | 74 ± 1.8** |

Note:
**$P < 0.01$,
***$P < 0.001$

The above results reveal that the polysaccharides of aloes have a high hypoglycemic effect.

The clinical tests on patients suffering diabetes by use of the composition of the present invention are shown.

CASE 1

Patient: D.T. 63-year-old man

Name of Disease: Diabetes

Treatment History: When he consulted a doctor, he had typical symptoms of diabetes, that is, unhealthy complexion, thirst feeling, thin body (39.2 Kg weight and 172 cm height), dizziness and oversensitiveness of feet and hands to the cold.

To this patient, when hungry, the polysaccharide obtained from *Aloe arborescens Mill.* in Example was orally administered continuously at a daily dosage of 300 mg in 3 separate doses over three months.

The result of biochemical test is shown in Table 1.

TABLE 1

| | Blood glucose* (mg/dl) | Urine glucose* (g/dl) | Urine protein* (mg/dl) |
|---|---|---|---|
| Before administration | 232 | 3.3 | 20 |
| One month later | 131 | 1.2 | 15 |
| Two months later | 109 | 0.95 | (−) |

TABLE 1-continued

|  | Blood glucose* (mg/dl) | Urine glucose* (g/dl) | Urine protein* (mg/dl) |
|---|---|---|---|
| Three months later** | 82 | 0.05 | (−) |

Note:
*All of the data are those when the patient is hungry.
**At this time, thirst feeling, dizziness and oversensitiveness disappeared and the body weight increased by 48 Kg and further the complexion was remarkably improved to the same extent as that of normal people.

CASE 2

Patient: T.T. 61-year-old man
Name of Disease: Diabetes and anemia
Treatment History: When he consulted a doctor, he had thirst feeling together with headache, shoulder stiffness and helplessness feeling.

The polysaccharide obtained from *Aloe vera L.* in Example was orally administered to this patient when hungry in the same manner as in the case 1 over four months.

The result of biochemical test is shown in Table 2.

TABLE 2

|  | Blood glucose* (mg/dl) | Urine glucose* (g/dl) | Urine protein* (mg/dl) |
|---|---|---|---|
| Before administration | 167 | 2.0 | (−) |
| Four months later** | 101 | (−) | (−) |

Note:
*All of the data are those when the patient is hungry.
**At this time, thirst feeling, headache, shoulder stiffness and helplessness feeling disappeared.

CASE 3

Patient: N.T. 43-year-old man
Name of Disease: Diabetes and pancreatic lithiasis
Treatment History: When he consulted a doctor, he complained of thirst feeling, decrease of vitality and oversensitiveness of feet and hands to the cold.

The polysaccharide obtained from *Aloe vera L.* in Example was orally administered to this patient when hungry in the same manner as in the case 1 over six months.

The result of biochemical test is shown in Table 3.

TABLE 3

|  | Blood glucose* (mg/dl) | Urine glucose* (g/dl) | Urine protein* (mg/dl) |
|---|---|---|---|
| Before administration | 213 | 3.2 | (−) |
| Six months later** | 108 | 0.1 | (−) |

Note:
*All of the data are those when the patient is hungry.
**At this time, thirst feeling, decrease of vitality and oversensitiveness of feet and hands to the cold disappeared.

CASE 4

Patient: H.K. 53-year-old woman
Name of Disease: Diabetes and liver complaint
Treatment History: She complained of thirst, severe oversensitiveness of feet and hands to the cold, shoulder stiffness and dizziness.

The polysaccharide obtained from *Aloe arborescens Mill.* in example was orally administered to the patient in the same manner as in the case 1 over 3 months.

The result of biochemical test is shown in Table 4.

TABLE 4

|  | Blood sugar* (mg/dl) | Urine sugar* (g/dl) | Urine protein* (mg/dl) |
|---|---|---|---|
| Before administration | 159 | 1.2 | (−) |
| Three months later** | 99 | (−) | (−) |

Note:
*All of the data are those when the patient is hungry.
**At this time, the above mentioned symptoms disappeared.

CASE 5

Patient: A.T. 45-year-old man
Name of Disease: Diabetes
Treatment History: He complained of thirst, shoulder stiffness and decrease of vitality.

The polysaccharide obtained from *Aloe arborescens Mill.* in example was orally administered to the patient in the same manner as in the above case 1 over six months.

Table 5 shows the results of biochemical test.

TABLE 5

|  | Blood glucose* (mg/dl) | Urine glucose* (g/dl) | Urine protein* (mg/dl) |
|---|---|---|---|
| Before administration | 172 | 2.5 | (−) |
| Six months later** | 104 | (−) | (−) |

Note:
*All of the data are those when the patient is hungry.
**At this time, the above symptoms disappeared.

What is claimed is:

1. A method of treating diabetes which comprises administering to a patient afflicted with diabetes a therapeutically effective amount of a hypoglycemic composition which contains as an effective component a polysaccharide contained in aloes of the family Liliaceae and having hypoglycemic activity and water solubility.

2. The method of claim 1 wherein the aloe of the family Liliaceae is selected from the group of arborescent aloe (*Aloe arborescens Mill.*); cape aloes (*Aloe ferox Mill., Aloe vera L., Aloe africana Mill.*); nathal aloes (*Aloe barberae Dyer, Aloe soccotrina Lam.*); zanzibar aloe (*Aloe perryi Baker*); curacau aloe (*Aloe barbadensis Miller*); and jaffarabad aloes (*Aloe vera L. chinensis Haw., Aloe striatula Haw.*).

3. The method of claim 2 wherein the aloe of the family Liliaceae is an arborescent aloe (*Aloe arborescens Mill.*) or a cape aloe (*Aloe vera L.*).

4. The method of claim 1, wherein the aloe of the family Liliaceae is an arborescent aloe (*Aloe arborescens Mill.*) and the polysaccharide having hypoglycemic activity and water solubility has the following properties;

(i) infrared absorption spectrum (KBr method) $\nu$max: 3300, 1590, 1410, 1240, 1050 and 600 (broad) cm$^{-1}$;
(ii) ultraviolet absorption: $\lambda_{max}^{H2O}$ 275 nm $E_{1\,cm}^{0.01\%}$: 50; $\lambda_{max}^{H2O}$ 305 nm $E_{1\,cm}^{0.01\%}$: 50;
(iii) NMR spectrum (90 MHz, D$_2$O): 5.25(s), 5.21–4.35(m), 4.21(s), 3.92–3.45(m), 2.39(s), 2.07(s), 1.85(s), 1.50(s), 1.25(s);
(iv) pH: a pH of 4.95 when 100 mg of the product is dissolved in 10 ml of distilled water;
(v) decomposition temperature: 240° C.;
(vi) solubility: being soluble in water and insoluble in benzene, ether, chloroform, alcohols and acetone;

(vii) color reaction: developing a pale yellowish red color on contact with a mixture of 2% aqueous solution of phenol and concentrated sulfuric acid, and being positive for silver mirror reaction and Fehling's solution.

5. The method of claim 1, wherein the aloe of the family Liliaceae is a cape aloe (*Aloe vera L.*) and the polysaccharide having hypoglycemic activity and water solubility has the following properties:
(i) infrared absorption spectrum (KBr method) $\nu$max: 3370, 1730, 1600, 1235, and 1040 cm$^{-1}$;
(ii) ultraviolet absorption; $\lambda_{max}^{H2O}$ 275 nm $E_{1\,cm}^{0.05\%}$: 12; $\lambda_{max}^{H2O}$ 295 nm $E_{1\,cm}^{0.05\%}$: 12;
(iii) NMR spectrum (90 MHz, D$_2$O); 5.12(s), 5.03–4.64(m), 4.59(s), 4.43(s), 4.13(s), 3.49(s), 2.05(s), 1.88(s) 1.49(s) and 1.27(d, j=7);
(iv) pH: having a pH of 4.75 when 100 mg of the product is dissolved in 10 ml of distilled water;
(v) decomposition temperature 240° C.
(vi) solubility; being soluble in water and insoluble in benzene, ether, chloroform, alcohols and acetone;
(vii) color reaction; developing a pale yellowish red color on contact with a mixture of 2% aqueous solution of phenol and concentrated sulfuric acid, and being positive for silver mirror reaction and Fehling's solution.

* * * * *

UNITED STATES PATENT AND TRADEMARK OFFICE
CERTIFICATE OF CORRECTION

PATENT NO. : 4,598,069
DATED : July 1, 1986
INVENTOR(S) : Hiroshi Hikino et al.

It is certified that error appears in the above-identified patent and that said Letters Patent is hereby corrected as shown below:

The title should read:-- METHOD OF TREATING DIABETES USING ALOES POLYSACCHARIDES--

Column 1, line 62: "plane" should read --plant--

Column 2, line 57: "power" should read -- powder--

Column 3, line 22: "(36/32" should read --36/32--

Signed and Sealed this

Sixth Day of January, 1987

Attest:

DONALD J. QUIGG

Attesting Officer          Commissioner of Patents and Trademarks